United States Patent
Kushnir et al.

(10) Patent No.: US 10,241,119 B2
(45) Date of Patent: Mar. 26, 2019

(54) HIGH SENSITIVITY MEASUREMENT OF PARATHYROID HORMONE-RELATED PEPTIDE USING LC-MS/MS AND ASSOCIATED METHODS

(71) Applicant: University of Utah Research Foundation, Salt Lake City, UT (US)

(72) Inventors: Mark M. Kushnir, Salt Lake City, UT (US); Alan L. Rockwood, Riverton, UT (US); A. Wayne Meikle, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 38 days.

(21) Appl. No.: 15/150,416

(22) Filed: May 9, 2016

(65) Prior Publication Data
US 2016/0327577 A1 Nov. 10, 2016

Related U.S. Application Data

(60) Provisional application No. 62/179,488, filed on May 7, 2015.

(51) Int. Cl.
G01N 33/68 (2006.01)
G01N 33/78 (2006.01)
C07K 14/635 (2006.01)

(52) U.S. Cl.
CPC .......... *G01N 33/78* (2013.01); *C07K 14/635* (2013.01); *G01N 33/6848* (2013.01); *G01N 2333/635* (2013.01)

(58) Field of Classification Search
None
See application file for complete search history.

(56) References Cited

PUBLICATIONS

Zheng et al., Mass Spectrometric Immunoassay for Parathyroid Hormone Related Protein (PTHrP), 48th ASMS Conference on Mass Spectrometry and Allied Topics, Jun. 16, 2000 (Year: 2000).*
Bronsema et al., Internal standards in quantitative determination of protein biopharmaceuticals using liquid chromatography coupled to mass spectrometry, Journal of Chromatography B, 893-894 (2012), pp. 1-14 (Year: 2012).*
Kumar et al., Quantification of Serum 1-84 Parathyroid Hormone in Patients with Hyperparathyroidism by Immunocapture In Situ Digestion Liquid Chromatography—Tandem Mass Spectrometry, Clinical Chemistry 56:2 306-313 (2010) (Year: 2010).*
Menegasso, Development of the MALDI technique Imaging utilizing animal tissues, Thesis, Institute of Bioscience, Translation, (Year: 2010).*
Burtis, Parathyroid Hormone-Related Protein: Structure, Function and Measurement, Clinical Chemistry, 38/11, 2171-2183, 1992 (Year: 1992).*
PTHrP UniProt Entry, 2018 (Year: 2018).*
Megasso-translated, English translation of the Menegasso reference, (Year: 2010).*
Cho et al., Quantitative selection and parallel characterization of aptamers, PNAS, vol. 110, No. 46, Nov. 12, 2013.*
Silantes Media for growth of *E. coli* and yeast, Stable Isotope labeled OD Media, Webpage, Aug. 20, 2008.*

* cited by examiner

*Primary Examiner* — Taeyoon Kim
*Assistant Examiner* — Srikanth Patury
(74) *Attorney, Agent, or Firm* — Thorpe North & Western, LLP

(57) ABSTRACT

Methods for measuring and analyzing parathyroid hormone-related peptide (PTHrP) using LC-MS/MS, including applications of the methods thereof, are disclosed and discussed. Such methods can include, along with the use of an isotope-labeled internal standard, purifying PTHrP from a biological sample, proteolytically digesting the PTHrP, and measuring specific digestion products using the using LC-MS/MS.

16 Claims, 6 Drawing Sheets
Specification includes a Sequence Listing.

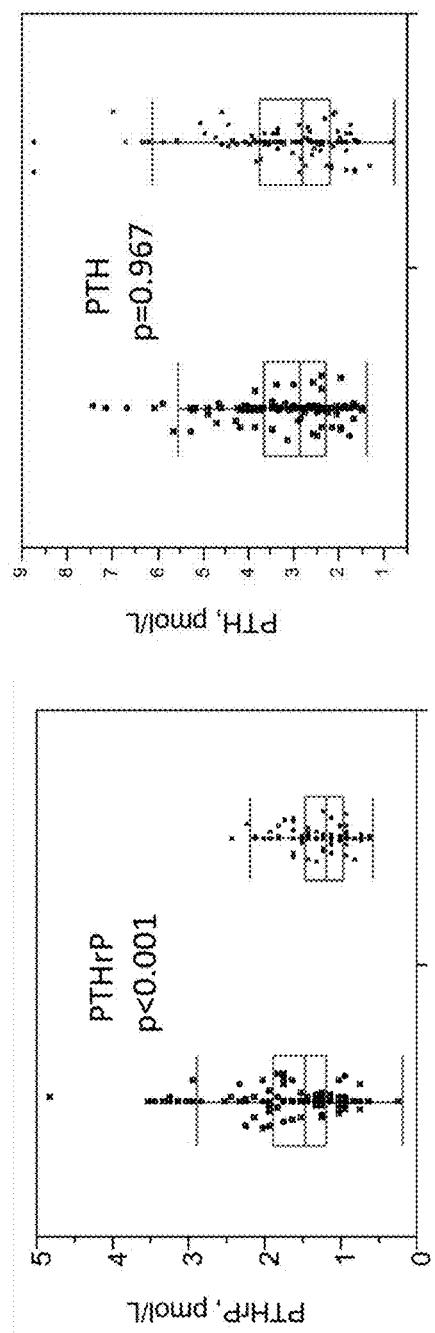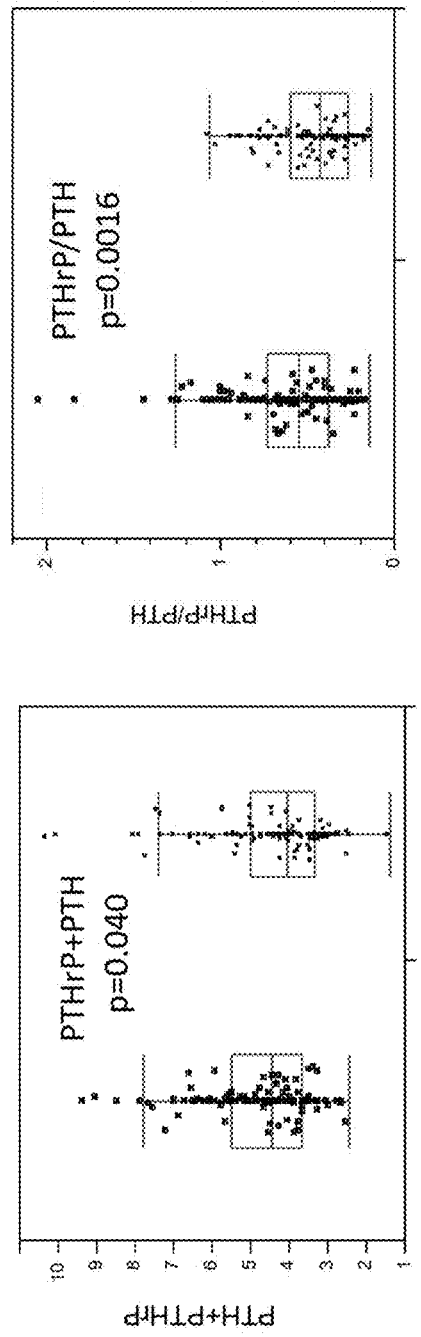
FIG. 4A  FIG. 4B  FIG. 4C  FIG. 4D

```
                          SEQUENCE LISTING

<160> NUMBER OF SEQ ID NOS: 40

<210> SEQ ID NO 1
<211> LENGTH: 86
<212> TYPE: PRT
<213> ORGANISM: Homo sapiens

<400> SEQUENCE: 1

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile Arg Ala Thr Ser Glu Val Ser Pro Asn Ser Lys Pro
        35                  40                  45

Ser Pro Asn Thr Lys Asn His Pro Val Arg Phe Gly Ser Asp Asp Glu
    50                  55                  60

Gly Arg Tyr Leu Thr Gln Glu Thr Asn Lys Val Glu Thr Tyr Lys Glu
65                  70                  75                  80

Gln Pro Leu Lys Thr Pro
                85

<210> SEQ ID NO 2
<211> LENGTH: 8
<212> TYPE: PRT
<213> ORGANISM: Homo sapiens

<400> SEQUENCE: 2

Tyr Leu Thr Gln Glu Thr Asn Lys
1               5

<210> SEQ ID NO 3
<211> LENGTH: 6
<212> TYPE: PRT
<213> ORGANISM: Homo sapiens

<400> SEQUENCE: 3

Ser Ile Gln Asp Leu Arg
1               5

<210> SEQ ID NO 4
<211> LENGTH: 11
<212> TYPE: PRT
<213> ORGANISM: Homo sapiens

<400> SEQUENCE: 4

Ala Val Ser Glu His Gln Leu Leu His Asp Lys
1               5                   10
```

```
<210> SEQ ID NO 5
<211> LENGTH: 16
<212> TYPE: PRT
<213> ORGANISM: Homo sapiens

<400> SEQUENCE: 5

Phe Phe Leu His His Leu Ile Ala Glu Ile His Thr Ala Glu Ile Arg
1               5                   10                  15

<210> SEQ ID NO 6
<211> LENGTH: 8
<212> TYPE: PRT
<213> ORGANISM: Homo sapiens

<400> SEQUENCE: 6

Phe Gly Ser Asp Asp Glu Gly Arg
1               5

<210> SEQ ID NO 7
<211> LENGTH: 10
<212> TYPE: PRT
<213> ORGANISM: Homo sapiens

<400> SEQUENCE: 7

Ala Thr Ser Glu Val Ser Pro Asn Ser Lys
1               5                   10

<210> SEQ ID NO 8
<211> LENGTH: 6
<212> TYPE: PRT
<213> ORGANISM: Homo sapiens

<400> SEQUENCE: 8

Pro Ser Pro Asn Thr Lys
1               5

<210> SEQ ID NO 9
<211> LENGTH: 5
<212> TYPE: PRT
<213> ORGANISM: Homo sapiens

<400> SEQUENCE: 9

Asn His Pro Val Arg
1               5

<210> SEQ ID NO 10
<211> LENGTH: 5
<212> TYPE: PRT
<213> ORGANISM: Homo sapiens

<400> SEQUENCE: 10

Val Glu Thr Tyr Lys
1               5

<210> SEQ ID NO 11
<211> LENGTH: 5
<212> TYPE: PRT
<213> ORGANISM: Homo sapiens

<400> SEQUENCE: 11

Glu Gln Pro Leu Lys
1               5

<210> SEQ ID NO 12
<211> LENGTH: 75
```

<212> TYPE: PRT
<213> ORGANISM: Homo sapiens

<400> SEQUENCE: 12

Gly Lys Ser Ile Gln Asp Leu Arg Arg Phe Phe Leu His His Leu
1               5                   10                  15

Ile Ala Glu Ile His Thr Ala Glu Ile Arg Ala Thr Ser Glu Val Ser
            20                  25                  30

Pro Asn Ser Lys Pro Ser Pro Asn Thr Lys Asn His Pro Val Arg Phe
        35                  40                  45

Gly Ser Asp Asp Glu Gly Arg Tyr Leu Thr Gln Glu Thr Asn Lys Val
    50                  55                  60

Glu Thr Tyr Lys Glu Gln Pro Leu Lys Thr Pro
65                  70                  75

<210> SEQ ID NO 13
<211> LENGTH: 73
<212> TYPE: PRT
<213> ORGANISM: Homo sapiens

<400> SEQUENCE: 13

Ser Ile Gln Asp Leu Arg Arg Phe Phe Leu His His Leu Ile Ala
1               5                   10                  15

Glu Ile His Thr Ala Glu Ile Arg Ala Thr Ser Glu Val Ser Pro Asn
            20                  25                  30

Ser Lys Pro Ser Pro Asn Thr Lys Asn His Pro Val Arg Phe Gly Ser
        35                  40                  45

Asp Asp Glu Gly Arg Tyr Leu Thr Gln Glu Thr Asn Lys Val Glu Thr
    50                  55                  60

Tyr Lys Glu Gln Pro Leu Lys Thr Pro
65                  70

<210> SEQ ID NO 14
<211> LENGTH: 67
<212> TYPE: PRT
<213> ORGANISM: Homo sapiens

<400> SEQUENCE: 14

Arg Arg Phe Phe Leu His His Leu Ile Ala Glu Ile His Thr Ala Glu
1               5                   10                  15

Ile Arg Ala Thr Ser Glu Val Ser Pro Asn Ser Lys Pro Ser Pro Asn
            20                  25                  30

Thr Lys Asn His Pro Val Arg Phe Gly Ser Asp Asp Glu Gly Arg Tyr
        35                  40                  45

Leu Thr Gln Glu Thr Asn Lys Val Glu Thr Tyr Lys Glu Gln Pro Leu
    50                  55                  60

Lys Thr Pro
65

<210> SEQ ID NO 15
<211> LENGTH: 66
<212> TYPE: PRT
<213> ORGANISM: Homo sapiens

<400> SEQUENCE: 15

Arg Phe Phe Leu His His Leu Ile Ala Glu Ile His Thr Ala Glu Ile
1               5                   10                  15

Arg Ala Thr Ser Glu Val Ser Pro Asn Ser Lys Pro Ser Pro Asn Thr
            20                  25                  30

Lys Asn His Pro Val Arg Phe Gly Ser Asp Asp Glu Gly Arg Tyr Leu
            35                  40                  45

Thr Gln Glu Thr Asn Lys Val Glu Thr Tyr Lys Gln Pro Leu Lys
    50                  55                  60

Thr Pro
65

<210> SEQ ID NO 16
<211> LENGTH: 65
<212> TYPE: PRT
<213> ORGANISM: Homo sapiens

<400> SEQUENCE: 16

Phe Phe Leu His His Leu Ile Ala Glu Ile His Thr Ala Glu Ile Arg
1               5                   10                  15

Ala Thr Ser Glu Val Ser Pro Asn Ser Lys Pro Ser Pro Asn Thr Lys
            20                  25                  30

Asn His Pro Val Arg Phe Gly Ser Asp Asp Glu Gly Arg Tyr Leu Thr
            35                  40                  45

Gln Glu Thr Asn Lys Val Glu Thr Tyr Lys Gln Pro Leu Lys Thr
    50                  55                  60

Pro
65

<210> SEQ ID NO 17
<211> LENGTH: 49
<212> TYPE: PRT
<213> ORGANISM: Homo sapiens

<400> SEQUENCE: 17

Ala Thr Ser Glu Val Ser Pro Asn Ser Lys Pro Ser Pro Asn Thr Lys
1               5                   10                  15

Asn His Pro Val Arg Phe Gly Ser Asp Asp Glu Gly Arg Tyr Leu Thr
            20                  25                  30

Gln Glu Thr Asn Lys Val Glu Thr Tyr Lys Gln Pro Leu Lys Thr
        35                  40                  45

Pro

<210> SEQ ID NO 18
<211> LENGTH: 39
<212> TYPE: PRT
<213> ORGANISM: Homo sapiens

<400> SEQUENCE: 18

Pro Ser Pro Asn Thr Lys Asn His Pro Val Arg Phe Gly Ser Asp Asp
1               5                   10                  15

Glu Gly Arg Tyr Leu Thr Gln Glu Thr Asn Lys Val Glu Thr Tyr Lys
            20                  25                  30

Glu Gln Pro Leu Lys Thr Pro
        35

<210> SEQ ID NO 19
<211> LENGTH: 33
<212> TYPE: PRT
<213> ORGANISM: Homo sapiens

<400> SEQUENCE: 19

Asn His Pro Val Arg Phe Gly Ser Asp Asp Glu Gly Arg Tyr Leu Thr
1               5                   10                  15

```
Gln Glu Thr Asn Lys Val Glu Thr Tyr Lys Glu Gln Pro Leu Lys Thr
            20                  25                  30
Pro

<210> SEQ ID NO 20
<211> LENGTH: 28
<212> TYPE: PRT
<213> ORGANISM: Homo sapiens

<400> SEQUENCE: 20

Phe Gly Ser Asp Asp Glu Gly Arg Tyr Leu Thr Gln Glu Thr Asn Lys
1               5                   10                  15

Val Glu Thr Tyr Lys Glu Gln Pro Leu Lys Thr Pro
            20                  25

<210> SEQ ID NO 21
<211> LENGTH: 73
<212> TYPE: PRT
<213> ORGANISM: Homo sapiens

<400> SEQUENCE: 21

Gly Lys Ser Ile Gln Asp Leu Arg Arg Arg Phe Phe Leu His His Leu
1               5                   10                  15

Ile Ala Glu Ile His Thr Ala Glu Ile Arg Ala Thr Ser Glu Val Ser
            20                  25                  30

Pro Asn Ser Lys Pro Ser Pro Asn Thr Lys Asn His Pro Val Arg Phe
        35                  40                  45

Gly Ser Asp Asp Glu Gly Arg Tyr Leu Thr Gln Glu Thr Asn Lys Val
    50                  55                  60

Glu Thr Tyr Lys Glu Gln Pro Leu Lys
65                  70

<210> SEQ ID NO 22
<211> LENGTH: 71
<212> TYPE: PRT
<213> ORGANISM: Homo sapiens

<400> SEQUENCE: 22

Ser Ile Gln Asp Leu Arg Arg Arg Phe Phe Leu His His Leu Ile Ala
1               5                   10                  15

Glu Ile His Thr Ala Glu Ile Arg Ala Thr Ser Glu Val Ser Pro Asn
            20                  25                  30

Ser Lys Pro Ser Pro Asn Thr Lys Asn His Pro Val Arg Phe Gly Ser
        35                  40                  45

Asp Asp Glu Gly Arg Tyr Leu Thr Gln Glu Thr Asn Lys Val Glu Thr
    50                  55                  60

Tyr Lys Glu Gln Pro Leu Lys
65                  70

<210> SEQ ID NO 23
<211> LENGTH: 65
<212> TYPE: PRT
<213> ORGANISM: Homo sapiens

<400> SEQUENCE: 23

Arg Arg Phe Phe Leu His His Leu Ile Ala Glu Ile His Thr Ala Glu
1               5                   10                  15

Ile Arg Ala Thr Ser Glu Val Ser Pro Asn Ser Lys Pro Ser Pro Asn
            20                  25                  30
```

Thr Lys Asn His Pro Val Arg Phe Gly Ser Asp Asp Glu Gly Arg Tyr
            35                  40                  45

Leu Thr Gln Glu Thr Asn Lys Val Glu Thr Tyr Lys Glu Gln Pro Leu
 50                  55                  60

Lys
 65

<210> SEQ ID NO 24
<211> LENGTH: 64
<212> TYPE: PRT
<213> ORGANISM: Homo sapiens

<400> SEQUENCE: 24

Arg Phe Phe Leu His His Leu Ile Ala Glu Ile His Thr Ala Glu Ile
 1               5                  10                  15

Arg Ala Thr Ser Glu Val Ser Pro Asn Ser Lys Pro Ser Pro Asn Thr
             20                  25                  30

Lys Asn His Pro Val Arg Phe Gly Ser Asp Asp Glu Gly Arg Tyr Leu
         35                  40                  45

Thr Gln Glu Thr Asn Lys Val Glu Thr Tyr Lys Glu Gln Pro Leu Lys
 50                  55                  60

<210> SEQ ID NO 25
<211> LENGTH: 63
<212> TYPE: PRT
<213> ORGANISM: Homo sapiens

<400> SEQUENCE: 25

Phe Phe Leu His His Leu Ile Ala Glu Ile His Thr Ala Glu Ile Arg
 1               5                  10                  15

Ala Thr Ser Glu Val Ser Pro Asn Ser Lys Pro Ser Pro Asn Thr Lys
             20                  25                  30

Asn His Pro Val Arg Phe Gly Ser Asp Asp Glu Gly Arg Tyr Leu Thr
         35                  40                  45

Gln Glu Thr Asn Lys Val Glu Thr Tyr Lys Glu Gln Pro Leu Lys
 50                  55                  60

<210> SEQ ID NO 26
<211> LENGTH: 47
<212> TYPE: PRT
<213> ORGANISM: Homo sapiens

<400> SEQUENCE: 26

Ala Thr Ser Glu Val Ser Pro Asn Ser Lys Pro Ser Pro Asn Thr Lys
 1               5                  10                  15

Asn His Pro Val Arg Phe Gly Ser Asp Asp Glu Gly Arg Tyr Leu Thr
             20                  25                  30

Gln Glu Thr Asn Lys Val Glu Thr Tyr Lys Glu Gln Pro Leu Lys
         35                  40                  45

<210> SEQ ID NO 27
<211> LENGTH: 37
<212> TYPE: PRT
<213> ORGANISM: Homo sapiens

<400> SEQUENCE: 27

Pro Ser Pro Asn Thr Lys Asn His Pro Val Arg Phe Gly Ser Asp Asp
 1               5                  10                  15

Glu Gly Arg Tyr Leu Thr Gln Glu Thr Asn Lys Val Glu Thr Tyr Lys

Glu Gln Pro Leu Lys
                35

<210> SEQ ID NO 28
<211> LENGTH: 31
<212> TYPE: PRT
<213> ORGANISM: Homo sapiens

<400> SEQUENCE: 28

Asn His Pro Val Arg Phe Gly Ser Asp Asp Glu Gly Arg Tyr Leu Thr
1               5                   10                  15
Gln Glu Thr Asn Lys Val Glu Thr Tyr Lys Glu Gln Pro Leu Lys
                20                  25                  30

<210> SEQ ID NO 29
<211> LENGTH: 26
<212> TYPE: PRT
<213> ORGANISM: Homo sapiens

<400> SEQUENCE: 29

Phe Gly Ser Asp Asp Glu Gly Arg Tyr Leu Thr Gln Glu Thr Asn Lys
1               5                   10                  15
Val Glu Thr Tyr Lys Glu Gln Pro Leu Lys
                20                  25

<210> SEQ ID NO 30
<211> LENGTH: 68
<212> TYPE: PRT
<213> ORGANISM: Homo sapiens

<400> SEQUENCE: 30

Gly Lys Ser Ile Gln Asp Leu Arg Arg Arg Phe Phe Leu His His Leu
1               5                   10                  15
Ile Ala Glu Ile His Thr Ala Glu Ile Arg Ala Thr Ser Glu Val Ser
                20                  25                  30
Pro Asn Ser Lys Pro Ser Pro Asn Thr Lys Asn His Pro Val Arg Phe
                35                  40                  45
Gly Ser Asp Asp Glu Gly Arg Tyr Leu Thr Gln Glu Thr Asn Lys Val
        50                  55                  60
Glu Thr Tyr Lys
65

<210> SEQ ID NO 31
<211> LENGTH: 66
<212> TYPE: PRT
<213> ORGANISM: Homo sapiens

<400> SEQUENCE: 31

Ser Ile Gln Asp Leu Arg Arg Arg Phe Phe Leu His His Leu Ile Ala
1               5                   10                  15
Glu Ile His Thr Ala Glu Ile Arg Ala Thr Ser Glu Val Ser Pro Asn
                20                  25                  30
Ser Lys Pro Ser Pro Asn Thr Lys Asn His Pro Val Arg Phe Gly Ser
                35                  40                  45
Asp Asp Glu Gly Arg Tyr Leu Thr Gln Glu Thr Asn Lys Val Glu Thr
        50                  55                  60
Tyr Lys
65

<210> SEQ ID NO 32
<211> LENGTH: 60
<212> TYPE: PRT
<213> ORGANISM: Homo sapiens

<400> SEQUENCE: 32

Arg Arg Phe Phe Leu His His Leu Ile Ala Glu Ile His Thr Ala Glu
1               5                   10                  15

Ile Arg Ala Thr Ser Glu Val Ser Pro Asn Ser Lys Pro Ser Pro Asn
            20                  25                  30

Thr Lys Asn His Pro Val Arg Phe Gly Ser Asp Asp Glu Gly Arg Tyr
        35                  40                  45

Leu Thr Gln Glu Thr Asn Lys Val Glu Thr Tyr Lys
    50                  55                  60

<210> SEQ ID NO 33
<211> LENGTH: 59
<212> TYPE: PRT
<213> ORGANISM: Homo sapiens

<400> SEQUENCE: 33

Arg Phe Phe Leu His His Leu Ile Ala Glu Ile His Thr Ala Glu Ile
1               5                   10                  15

Arg Ala Thr Ser Glu Val Ser Pro Asn Ser Lys Pro Ser Pro Asn Thr
            20                  25                  30

Lys Asn His Pro Val Arg Phe Gly Ser Asp Asp Glu Gly Arg Tyr Leu
        35                  40                  45

Thr Gln Glu Thr Asn Lys Val Glu Thr Tyr Lys
    50                  55

<210> SEQ ID NO 34
<211> LENGTH: 58
<212> TYPE: PRT
<213> ORGANISM: Homo sapiens

<400> SEQUENCE: 34

Phe Phe Leu His His Leu Ile Ala Glu Ile His Thr Ala Glu Ile Arg
1               5                   10                  15

Ala Thr Ser Glu Val Ser Pro Asn Ser Lys Pro Ser Pro Asn Thr Lys
            20                  25                  30

Asn His Pro Val Arg Phe Gly Ser Asp Asp Glu Gly Arg Tyr Leu Thr
        35                  40                  45

Gln Glu Thr Asn Lys Val Glu Thr Tyr Lys
    50                  55

<210> SEQ ID NO 35
<211> LENGTH: 42
<212> TYPE: PRT
<213> ORGANISM: Homo sapiens

<400> SEQUENCE: 35

Ala Thr Ser Glu Val Ser Pro Asn Ser Lys Pro Ser Pro Asn Thr Lys
1               5                   10                  15

Asn His Pro Val Arg Phe Gly Ser Asp Asp Glu Gly Arg Tyr Leu Thr
            20                  25                  30

Gln Glu Thr Asn Lys Val Glu Thr Tyr Lys
        35                  40

<210> SEQ ID NO 36

```
<211> LENGTH: 32
<212> TYPE: PRT
<213> ORGANISM: Homo sapiens

<400> SEQUENCE: 36

Pro Ser Pro Asn Thr Lys Asn His Pro Val Arg Phe Gly Ser Asp Asp
1               5                   10                  15

Glu Gly Arg Tyr Leu Thr Gln Glu Thr Asn Lys Val Glu Thr Tyr Lys
            20                  25                  30

<210> SEQ ID NO 37
<211> LENGTH: 26
<212> TYPE: PRT
<213> ORGANISM: Homo sapiens

<400> SEQUENCE: 37

Asn His Pro Val Arg Phe Gly Ser Asp Asp Glu Gly Arg Tyr Leu Thr
1               5                   10                  15

Gln Glu Thr Asn Lys Val Glu Thr Tyr Lys
            20                  25

<210> SEQ ID NO 38
<211> LENGTH: 21
<212> TYPE: PRT
<213> ORGANISM: Homo sapiens

<400> SEQUENCE: 38

Phe Gly Ser Asp Asp Glu Gly Arg Tyr Leu Thr Gln Glu Thr Asn Lys
1               5                   10                  15

Val Glu Thr Tyr Lys
            20

<210> SEQ ID NO 39
<211> LENGTH: 20
<212> TYPE: PRT
<213> ORGANISM: Homo sapiens

<400> SEQUENCE: 39

Ser Asp Asp Glu Gly Arg Tyr Leu Thr Gln Glu Thr Asn Lys Val Glu
1               5                   10                  15

Thr Tyr Lys Glu
            20

<210> SEQ ID NO 40
<211> LENGTH: 17
<212> TYPE: PRT
<213> ORGANISM: Homo sapiens

<400> SEQUENCE: 40

Asp Asp Glu Gly Arg Tyr Leu Thr Gln Glu Thr Asn Lys Val Glu Thr
1               5                   10                  15

Tyr
```

HIGH SENSITIVITY MEASUREMENT OF PARATHYROID HORMONE-RELATED PEPTIDE USING LC-MS/MS AND ASSOCIATED METHODS

PRIORITY DATA

This application claims the benefit of U.S. Provisional Patent Application No. 62/179,488, filed on May 7, 2015 as entitled "High Sensitivity Measurement of Parathyroid Hormone Related Peptide Using LC-MS/MS and Applications of the Method" which is incorporated herein by reference in its entirety.

BACKGROUND

Parathyroid hormone-related peptide (PTHrP) is a member of the parathyroid hormone (PTH) family, sharing a close homology with PTH at the N-terminal sequence. Because both hormones bind to the same receptors, various physiological functions of PTHrP are similar to those of PTH. PTHrP functions as an autocrine, paracrine, and endocrine hormone, and is able to simulate most of the actions of PTH, including regulation of calcium ion homeostasis, bone resorption, distal tubular Ca reabsorption, and inhibition of proximal tubular phosphate transport. In health, PTHrP regulates bone development by maintaining the endochondral growth plate. It also plays a role during tooth eruption, development of mammary glands, pregnancy, fetal development, and regulation of Ca transfer to milk during lactation. Circulating concentrations of PTHrP in health are very low but can be increased during pregnancy and lactation and in some nonmalignant diseases.

BRIEF DESCRIPTION OF THE DRAWINGS

FIG. 4A is a graphical representation of data in accordance with one example.

FIG. 4B is a graphical representation of data in accordance with one example.

FIG. 4C is a graphical representation of data in accordance with one example.

FIG. 4D is a graphical representation of data in accordance with one example.

DESCRIPTION OF EMBODIMENTS

Figure 1A:
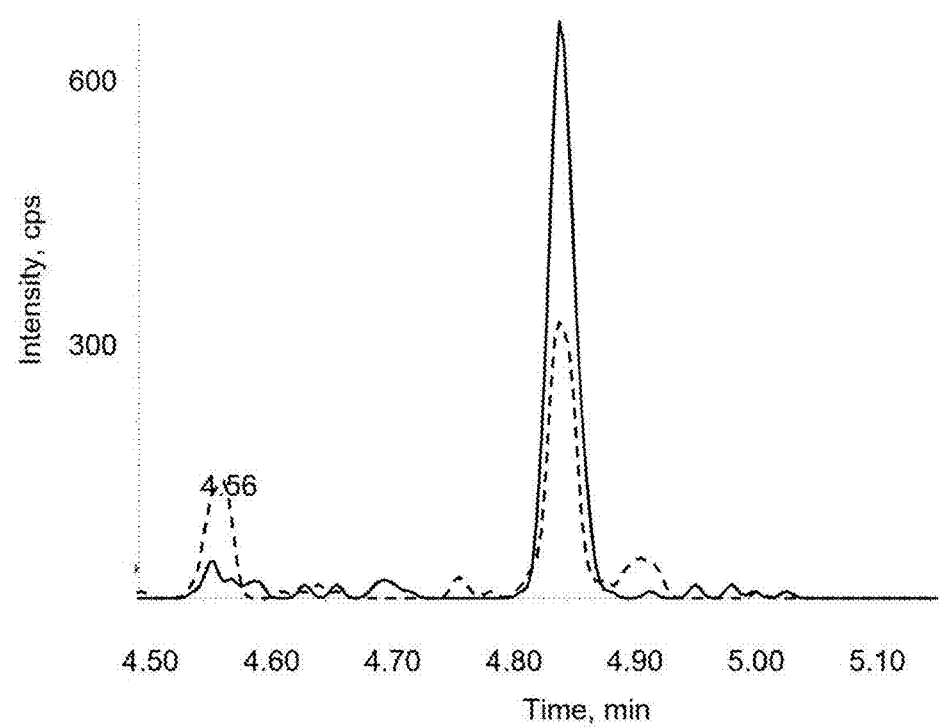
FIG. 1A is an MRM chromatogram of data in accordance with one example.

Although the following detailed description contains many specifics for the purpose of illustration, a person of ordinary skill in the art will appreciate that many variations and alterations to the following details can be made and are considered included herein.

Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used herein, the term "peptide" may be used to refer to a natural or synthetic molecule comprising two or more amino acids linked by the carboxyl group of one amino acid to the alpha amino group of another. A peptide of the present disclosure is not limited by length, and thus "peptide" can include polypeptides and proteins.

As use herein with respect to antibody-peptide interactions, the term "selective for" refers to a measurable and reproducible specific immunoreaction (i.e. the binding between a peptide and an antibody) that is determinative of the presence of the peptide in a biological sample or in a heterogeneous population of peptides and other biological components. Thus, under designated conditions, an antibody selective for a particular peptide does not bind in a significant amount to other peptides present in the sample.

As used herein, the term "antibody" comprises, but is not limited to, both naturally occurring and non-naturally occurring antibodies, including polyclonal and monoclonal antibodies, whole antibodies of any isotype (IgG, IgA, IgM, IgE, etc), and binding fragments thereof. The term "antibody" also includes chimeric antibodies, wholly synthetic antibodies, and fragments thereof. An antibody can be human, or that of another species including, for example, mouse, rabbit, goat, and the like.

As used herein, the term "biological sample" refers to any sample of a biological nature obtained from a subject that may contain a target peptide or other molecule of interest. Non-limiting examples include biological fluids and biological tissues such as blood, blood serum, plasma, saliva, semen, vaginal fluid, lymph, urine, lachrymal fluid, cancerous tissue, non-cancerous tissue, tumor tissue, skin tissue, and the like.

In this application, "comprises," "comprising," "containing" and "having" and the like can have the meaning ascribed to them in U.S. patent law and can mean "includes," "including," and the like, and are generally interpreted to be open ended terms. The terms "consisting of or" consists of are closed terms, and include only the components, structures, steps, or the like specifically listed in conjunction with such terms, as well as that which is in accordance with U.S. Patent law. "Consisting essentially of or" consists essentially of have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in this specification, like "comprising" or "including," it is understood that direct support should be afforded also to "consisting essentially of language as well as" consisting of language as if stated explicitly and vice versa.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

EXAMPLE EMBODIMENTS

An initial overview of technology embodiments is provided below and specific technology embodiments are then described in further detail. This initial summary is intended to aid readers in understanding the technology more quickly, but is not intended to identify key or essential technological features, nor is it intended to limit the scope of the claimed subject matter.

Parathyroid hormone-related protein (PTHrP) can be present at an elevated concentration in the blood of subjects diagnosed with breast, bladder, lung, uterus, and skin cancer, to name a few. PTHrP is known to activate pathways that allow tumor cells to form bone metastasis, a condition known as hypercalcemia (HC) of malignancy (HCM). In patients with HCM, parathyroid hormone (PTH) is typically suppressed due to elevated blood calcium, while uncontrolled release of PTHrP by tumor cells is responsible for the HC.

Radioimmunoassays (MA) are commonly used for the measurement of PTHrP, and a number of MA methods have been developed using antibodies raised against amino acid sequences (AAS) within the structure of PTHrP. Earlier researchers have observed that some of the healthy subjects had measurable concentrations of PTHrP, where reference intervals for healthy subjects were determined to be <2.6 pmol/L, and that concentrations of PTHrP were >2.6 pmol/L subjects with HCM. Other researchers reported, using two-site RIA, that the observed concentrations in healthy subjects were 0.8+/−0.01 pmol/L, and that the established upper limit of the normal was 1.1 pmol/L. Considering the observed very tight distribution of concentrations in healthy individuals (+/−0.01 pmol/L), performance of the method could be questioned. In another observation, the reported sensitivity of one RIA was 0.1 pmol/L, while 75% of subjects had undetectable PTHrP concentrations. In another example with subjects having HCM and solid-tumors, PTHrP concentrations were greater than 2.0 pmol/L. In yet another example, it was observed that 75% of subjects with bone metastases had elevated PTHrP concentrations, while the method was insufficiently sensitive to measure endogenous concentrations of PTHrP.

Two prior LC-MS/MS methods for PTHrP have been reported. The first (Lu et al.) is a method for quantitation of PTHrP (AAS 1-36), where the reported LOQ was 62 nmol/L. This method is insufficiently sensitive for diagnostic applications. The second (Washam et al.) is a qualitative SELDI-MS method for the detection of peptide PTHrP (AAS 12-48) in plasma of subjects with breast cancer. Based on the reported data, the presence of the peptide correlated with bone metastases in breast cancer subjects.

The present disclosure provides a high sensitivity/high specificity LC-MS/MS method for the analysis and measurement of PTHrP, as well as applications of PTHrP as a biomarker. It has been assumed in the art that PTHrP is not present in the blood of healthy subjects, and that PTHrP acts only within cells where it is produced, and on neighboring cells. It is becoming clear, however, that PTHrP is present in the blood of all people, and that these previous assumptions were the result of the low accuracy of PTHrP testing and testing conditions. The presently disclosed technology has a sufficiently high sensitivity to detect endogenous levels of PTHrP, such as, for example, 0.5 pmol/L or less. Such levels allow the detection of PTHrP across the reference intervals of PTHrP established by the present methodology of 0.5-2.3 pmol/L for male subjects, and 0.5-3.4 pmol/L for female subjects. Prior commercially available methods for testing PTHrP do not have sufficient sensitivity to measure concentrations for the vast majority of healthy subjects in the population.

In one example embodiment, a method of measuring PTHrP in a biological sample is provided. Such a method can include preparing the biological sample, which includes extracting PTHrP peptides from the biological sample, mixing a PTHrP sequence-derived isotope-labeled internal standard (IS) with the PTHrP peptides, proteolytically digesting the PTHrP peptides and the IS to produce a digestion product, and chromatographically separating the digestion product. The method can further include selecting and subjecting a chromatographic peak from the separated digestion product to tandem mass spectrometry to determine the amount of a target peptide.

PTHrP has a sequence of (AAS 37-122; AVSEHQLLHD KGKSIQDLRR RFFLHHLIAE IHTAEIRATS EVSPNSKPSP NTKNHPVRFG SDDEGRYLTQ ETNKVETYKE QPLKTP (SEQ ID NO: 001)). The target peptide can be any peptide derived from PTHrP, and may be dependent on a particular proteolytic enzyme used to generate various peptide fragments. Non-limiting examples of target peptides can include YLTQETNK (SEQ ID NO: 002), SIQDLR (SEQ ID NO: 003), AVSEHQLLHD K (SEQ ID NO: 004), FFLHHLIAEI HTAEIR (SEQ ID NO: 005), FGSDDEGR (SEQ ID NO: 006), ATSEVSPNSK (SEQ ID NO: 007), PSPNTK (SEQ ID NO: 008), NHPVR (SEQ ID NO: 009), VETYK (SEQ ID NO: 010), EQPLK (SEQ ID NO: 011), and the like, including combinations thereof. The target peptide can additionally include a peptide having a sequence listed in Table 1.

In one example embodiment, the IS can include AVSEHQLLHD KGKSIQDLRR RFFLHHLIAE IHTAEIRATS EVSPNSKPSP NTKNHPVRFG SDDEGRYLTQ ETNKVETYKE QPLKTP (SEQ ID NO: 001), or a fragment thereof. The isotope label of the IS can be any useful isotope that can be incorporated into a peptide. The IS can include any number of labeled amino acids, with each amino acid including any number of labeled atoms. For example, in one embodiment the IS includes at least one amino acid having at least one incorporated isotopic atoms. In another embodiment, the IS includes at least one amino acid having at least three incorporated isotopic atoms. Useful isotopes can include, without limitation, $^{13}C$ $^{15}N$, $^{18}O$, $^{2}H$, and thelike, including combinations thereof. It is noted that each labeled amino acid can include one or more species of isotopic label. In some embodiments, all or nearly all of a given atom can be isotopically labeled in any number of amino acids of the IS, including all amino acids.

In some embodiments, the IS can include a fragment of PTHrP. In such cases, the PTHrP fragment can include one or more labeled atoms as described. In one example, the IS can include a labeled fragment such as, without limitation, YLTQETNK (SEQ ID NO: 002), SIQDLR (SEQ ID NO: 003), AVSEHQLLHD K (SEQ ID NO: 004), FFLHHLIAEI HTAEIR (SEQ ID NO: 005), FGSDDEGR (SEQ ID NO: 006), ATSEVSPNSK (SEQ ID NO: 007), PSPNTK (SEQ ID NO: 008), NHPVR (SEQ ID NO: 009), VETYK (SEQ ID NO: 010), EQPLK (SEQ ID NO: 011), and the like, including combinations thereof. In another non-limiting example, the IS can include a labeled peptide from Table 1. Furthermore, in other embodiments, the IS may not be digested, and can be added following digesting the PTHrP peptides. In other embodiments, the IS can be added prior to digestion and following digestion.

TABLE 1

| | |
|---|---|
| SEQ ID NO: 012 | GKSIQDLRRRFFLHHLIAEIHTAEIRATSEVSPNS KPSPNTKNHPVRFGSDDEGRYLTQETNKVETYKEQ PLKTP |
| SEQ ID NO: 013 | SIQDLRRRFFLHHLIAEIHTAEIRATSEVSPNSKP SPNTKNHPVRFGSDDEGRYLTQETNKVETYKEQPL KTP |
| SEQ ID NO: 014 | RRFFLHHLIAEIHTAEIRATSEVSPNSKPSPNTKN HPVRFGSDDEGRYLTQETNKVETYKEQPLKTP |
| SEQ ID NO: 015 | RFFLHHLIAEIHTAEIRATSEVSPNSKPSPNTKNH PVRFGSDDEGRYLTQETNKVETYKEQPLKTP |
| SEQ ID NO: 016 | FFLHHLIAEIHTAEIRATSEVSPNSKPSPNTKNHP VRFGSDDEGRYLTQETNKVETYKEQPLKTP |
| SEQ ID NO: 017 | ATSEVSPNSKPSPNTKNHPVRFGSDDEGRYLTQET NKVETYKEQPLKTP |
| SEQ ID NO: 018 | PSPNTKNHPVRFGSDDEGRYLTQETNKVETYKEQP LKTP |
| SEQ ID NO: 019 | NHPVRFGSDDEGRYLTQETNKVETYKEQPLKTP |
| SEQ ID NO: 020 | FGSDDEGRYLTQETNKVETYKEQPLKTP |
| SEQ ID NO: 021 | GKSIQDLRRRFFLHHLIAEIHTAEIRATSEVSP NSKPSPNTKNHPVRFGSDDEGRYLTQETNKVET YKEQPLK |
| SEQ ID NO: 022 | SIQDLRRRFFLHHLIAEIHTAEIRATSEVSPNS KPSPNTKNHPVRFGSDDEGRYLTQETNKVETYK EQPLK |
| SEQ ID NO: 023 | RRFFLHHLIAEIHTAEIRATSEVSPNSKPSPNT KNHPVRFGSDDEGRYLTQETNKVETYKEQPLK |
| SEQ ID NO: 024 | RFFLHHLIAEIHTAEIRATSEVSPNSKPSPNTK NHPVRFGSDDEGRYLTQETNKVETYKEQPLK |
| SEQ ID NO: 025 | FFLHHLIAEIHTAEIRATSEVSPNSKPSPNTKN HPVRFGSDDEGRYLTQETNKVETYKEQPLK |
| SEQ ID NO: 026 | ATSEVSPNSKPSPNTKNHPVRFGSDDEGRYLTQ ETNKVETYKEQPLK |
| SEQ ID NO: 027 | PSPNTKNHPVRFGSDDEGRYLTQETNKVETYKE QPLK |
| SEQ ID NO: 028 | NHPVRFGSDDEGRYLTQETNKVETYKEQPLK |
| SEQ ID NO: 029 | FGSDDEGRYLTQETNKVETYKEQPLK |
| SEQ ID NO: 030 | GKSIQDLRRRFFLHHLIAEIHTAEIRATSEVSPNS KPSPNTKNHPVRFGSDDEGRYLTQETNKVETYK |
| SEQ ID NO: 031 | SIQDLRRRFFLHHLIAEIHTAEIRATSEVSPNSKP SPNTKNHPVRFGSDDEGRYLTQETNKVETYK |
| SEQ ID NO: 032 | RRFFLHHLIAEIHTAEIRATSEVSPNSKPSPNTKN HPVRFGSDDEGRYLTQETNKVETYK |
| SEQ ID NO: 033 | RFFLHHLIAEIHTAEIRATSEVSPNSKPSPNTKNH PVRFGSDDEGRYLTQETNKVETYK |
| SEQ ID NO: 034 | FFLHHLIAEIHTAEIRATSEVSPNSKPSPNTKNHP VRFGSDDEGRYLTQETNKVETYK |
| SEQ ID NO: 035 | ATSEVSPNSKPSPNTKNHPVRFGSDDEGRYLTQET NKVETYK |
| SEQ ID NO: 036 | PSPNTKNHPVRFGSDDEGRYLTQETNKVETYK |

TABLE 1-continued

| SEQ ID NO: 037 | NHPVRFGSDDEGRYLTQETNKVETYK |
| --- | --- |
| SEQ ID NO: 038 | FGSDDEGRYLTQETNKVETYK |
| SEQ ID NO: 039 | SDDEGRYLTQETNKVETYKE |
| SEQ ID NO: 040 | DDEGRYLTQETNKVETY |

In one specific example, the labeled IS has the sequence YLTQETNK (SEQ ID NO: 002). In another example, the labeled IS has the sequence YLTQETNK (SEQ ID NO: 002), and has all amino acids labeled at all N atoms with $^{15}N$. Mass transitions of such an IS are about m/z 504→729 and about m/z 505→730. It is noted that, in reference to mass transitions, the term "about" indicates rounding to a whole number. In such cases, "about" can indicate a deviation of ±0.5 from the listed value. In another example, the labeled IS has the sequence YLTQETNK (SEQ ID NO: 002), and has mass transitions of m/z 504.25→729.35 and m/z 504.75→730.25.

In another specific example, the target peptide has the sequence YLTQETNK (SEQ ID NO: 002), and has mass transitions of about m/z 499→720 and about m/z 499→721. In another example, the target peptide has the sequence YLTQETNK (SEQ ID NO: 002), and has mass transitions of m/z 498.75→720.35 and m/z 499.25→721.35.

PTHrP is unstable in serum and plasma samples, and degrades within hours when exposed to ambient temperature. If enrichment of PTHrP during the sample preparation is performed as per commonly used RIA testing at room temperature, PTHrP would be at least partially degraded when the RIA test was performed, thus greatly reducing the effectiveness of the assay. The same is true for sample preparation regardless of the form of the assay. As such, it can be important to optimize the sample preparation to minimize degradation factors, such as limiting exposure times to ambient temperatures, selecting buffers and other preparation ingredients that minimize degradation, utilizing physical separation techniques, preparing samples with no alkylation or reduction reactions, among others. In one embodiment, the sample preparation is performed in less than 2 hours, or less than 1 hour, in order to minimize degradation of the PTHrP.

As one further example, high sensitivity may not be achieved using traditional chromatographic separation. In such cases, the present methodology utilizes two dimensional chromatographic separation techniques. Additionally, due to its highly unstable nature and short half-life, the measurement of the intact sequence or endogenously present fragments of PTHrP present in blood will not provide an adequate representation of the rates of PTHrP biosynthesis that are indicative of PTHrP-related conditions. By capturing and isolating PTHrP peptides from a biological sample such as blood, followed by enzymatic digestion to generate peptide fragments, highly sensitive and accurate measurements can be made for proper quantitative analysis.

As one example, the method can further include affinity extracting PTHrP peptides from the biological sample using any affinity extraction technique compatible with the present methodology. In one embodiment, for example, the affinity extraction can be antibody affinity extraction using an antibody selective for PTHrP. In one embodiment, the antibody is a polyclonal antibody specific for PTHrP. In another example, the antibody is a monoclonal antibody specific for PTHrP. Another example of an affinity extraction technique includes aptamer affinity binding. Aptamers are known in the art, and can be single stranded DNA or RNA molecules that can bind to pre-selected targets, including peptides such as PTHrP with high affinity and specificity.

Various techniques can be utilized with affinity capture, including coupling the binding molecule (e.g. antibody or aptamer) to a solid substrate, followed by collecting the substrate or removing the biological sample from the substrate, depending on the nature of the substrate. For example, the binding molecule can be coupled to a substrate such as magnetic beats, after which the magnetic beads can be mixed with the biological fluid. Following affinity binding of the PTHrP to the binding molecule, the beads can be collected and washed to remove the biological sample components therefrom.

In another embodiment, a test sample prepared for tandem mass spectrometry is provided, and can include a trypsin-digested PTHrP peptide extracted from a biological sample, and a PTHrP sequence-derived isotope-labeled IS. Non-limiting examples of PTHrP peptides can include YLTQETNK (SEQ ID NO: 002), SIQDLR (SEQ ID NO: 003), AVSEHQLLHD K (SEQ ID NO: 004), FFLHHLIAEI HTAEIR (SEQ ID NO: 005), FGSDDEGR (SEQ ID NO: 006), ATSEVSPNSK (SEQ ID NO: 007), PSPNTK (SEQ ID NO: 008), NHPVR (SEQ ID NO: 009), VETYK (SEQ ID NO: 010), EQPLK (SEQ ID NO: 011), and the like, including combinations thereof. The PTHrP peptide can additionally include a peptide having a sequence listed in Table 1. In one specific example, the test sample prepared for tandem mass spectrometry can include a trypsin-digested PTHrP peptide extracted from a biological sample and comprising or consisting of the sequence YLTQETNK (SEQ ID NO: 002), and a PTHrP sequence-derived isotope-labeled internal standard (IS) comprising or consisting of the sequence YLTQETNK (SEQ ID NO: 002).

Other non-limiting examples of isotope-labeled IS can include AVSEHQLLHD KGKSIQDLRR RFFLHHLIAE IHTAEIRATS EVSPNSKPSP NTKNHPVRFG SDDE-GRYLTQ ETNKVETYKE QPLKTP (SEQ ID NO: 001), YLTQETNK (SEQ ID NO: 002), SIQDLR (SEQ ID NO: 003), AVSEHQLLHD K (SEQ ID NO: 004), FFLHHLIAEI HTAEIR (SEQ ID NO: 005), FGSDDEGR (SEQ ID NO: 006), ATSEVSPNSK (SEQ ID NO: 007), PSPNTK (SEQ ID NO: 008), NHPVR (SEQ ID NO: 009), VETYK (SEQ ID NO: 010), EQPLK (SEQ ID NO: 011), and the like, including combinations thereof. The isotope-labeled IS can additionally include a peptide having a sequence listed in Table 1.

In one specific example, the isotope-labeled IS has the sequence YLTQETNK (SEQ ID NO: 002), and has mass transitions of about m/z 504→729 and about m/z 505→730. In another example, the labeled IS has the sequence YLTQETNK (SEQ ID NO: 002), and has mass transitions of m/z 504.25→729.35 and m/z 504.75→730.25. In another specific example, the PTHrP peptide has the sequence YLTQETNK
(SEQ ID NO: 002), and has mass transitions of about m/z 499→720 and about m/z 499→721. In another example, the PTHrP peptide has the sequence YLTQETNK (SEQ ID NO: 002), and has mass transitions of m/z 498.75→720.35 and m/z 499.25→721.35.

In another embodiment, a tandem mass spectrometry reaction product is provided of a peptide fragment of PTHrP having the sequence YLTQETNK (SEQ ID NO: 002), and having mass transitions of about m/z 499→720 and about m/z 499→721. In another embodiment, the mass transitions are m/z 498.75→720.35 and m/z 499.25→721.35.

Examples of various experimental details are described to provide a fuller understanding of the presently disclosed technology, and are not intended to be limiting.

Reagents, Standards

Internal standards (IS) of PTHrP can be prepared from recombinant PTHrP (AAS 37-122; AVSEHQLLHD KGK-SIQDLRR RFFLHHLIAE IHTAEIRATS EVSPNSKPSP NTKNHPVRFG SDDEGRYLTQ ETNKVETYKE QPLKTP (SEQ ID NO: 001)) purchased from PeproTech (Rocky Hill, N.J.)) in fetal bovine serum, lyophilized and stored frozen at −70° C. Working calibrators were prepared in 0.1% BSA, at concentrations 1, 2, 5, 10, and 30 pmol/L. Rabbit polyclonal anti-PTHrP antibody was purchased from PeproTech. Plasma quality control samples were pooled human plasma and contained 4 and 11 pmol/L of PTHrP. Various sequences can be utilized depending on the particular enzyme Recombinant $^{15}N$ labeled internal standard (IS) (SEQ ID NO: 001) was diluted in BSA to a concentration of 1 nmol/L and frozen at −20° C. until used. Trypsin (purity 99%, activity 15,000 BAEE units), Tris(hydroxymethyl)aminomethane (TRIS), (4-(2-hydroxyethyl)-1-piperazineethanesulfonic acid (HEPES), formic acid, and acetic acid were purchased from Sigma-Aldrich (St. Louis, Mo.). All other reagents were of the highest purity commercially available. Solvents were of HPLC grade, purchased from JT Baker (Phillipsburg, N.J.). Polyclonal rabbit anti-PTHrP antibody (PeproTech) was conjugated to Tosyl activated magnetic beads (Life Technologies, Carlsbad, Calif.) according to the manufacturer's recommendations. Briefly, the beads were washed with buffer and re-suspended in one molar ammonium sulfate solution containing 20 µg of the antibody per milligram of beads. Beads were incubated at 37° C. for 20 hours, washed and incubated for 1 hour with blocking buffer containing 0.5% BSA, and reconstituted to a concentration of 20 mg/mL.

Sample Preparation

Sample preparation was performed on a liquid handler Janus (Perkin Elmer, Calif.). To a 400 µL aliquot of plasma sample, 400 µL of HEPES buffer (pH 7.4) and 20 µL of IS were added, and the samples were incubated for 15 minutes. After the incubation, 5 µL of the magnetic beads suspension was added, and the samples were incubated with agitation at 10° C. for 3 h. The beads were washed three times with TRIS buffer (pH 7.4), and then 200 µL of 25 mM bicarbonate buffer and 10 µL of trypsin (4 µg/µL) were added. The samples were then incubated for 3 hours at 37° C.

After the digestion 10 µL of 10% formic acid was added to the samples, the tubes were vortexed, the samples were transferred in wells of a 96-well plate, and 70 µL aliquots were injected in LC-MS/MS. Magnetic beads were processed using a magnetic stand for 96-well plates. The digestion conditions were optimized to ensure complete and reproducible digestion of PTHrP. Experiments showed no effect of the denaturing, cysteines reduction and alkylation on the recovery of the targeted peptide, and therefore reduction and alkylation were not used in this method.

Instrumental Analysis

Two-dimensional (2D) HPLC separation was performed on an HPLC system including series 1260 and 1290 pumps (Agilent Technologies, Santa Clara, Calif.). A Synergy Polar RP, 50×3 mm, 4 µm HPLC column (Phenomemex, Torrance, Calif.) was used for the $1^{st}$ D separation with gradient: 99% to 87% A in 2.7 min (A, 10 mM formic acid in water; B, 10 mM formic acid in acetonitrile); the $2^{nd}$ D separation was on a Synergy Max-RP, 100×3 mm, 2.5 µm, column (Phenomemex) using gradient 97% to 85% A in 2 min (A, 5 mM acetic acid in water; B, 5 mM acetic acid in acetonitrile); the LC separation was performed at 40° C.

Quantitative analysis was performed on an AB5500 mass spectrometer (AB Sciex, Framingham, Mass.) with a V-spray ionization source in a positive ion, multiple reaction monitoring (MRM) mode. Mass transitions monitored were m/z 498.75→720.35, 499.25→721.35, for the YLTQETNK peptide (SEQ ID NO: 002), and m/z 504.25→729.35, 504.75→730.25, for the IS (SEQ ID NO: 001). The instrument settings were adjusted to maximize the sensitivity and the specificity of detection. The heating gas temperature was 650° C.; the nebulizing, curtain and collision gases (nitrogen) were 60 psi, 60 psi, and 9 arbitrary units. The declustering potential, collision energy, collision cell exit potential, and entrance potential were 60V, 23V, 26V, and 10V. The dwell time for the mass transitions was 40 ms. The Q1 and Q3 quadrupoles were set to unit resolution (0.7 Da). The total analysis time per sample was 6.5 min. The instrument control and the data were performed using Analyst 1.5.2 (AB Sciex). Qualitative confirmation of PTHrP was assessed through the ratio of the concentrations determined from two mass transitions of the targeted peptide and the IS.

The stated limit of quantitation (LOQ) and the reference interval of the PTHrP RIA (Immunotech, Prague, Czech Republic) were 2 pmol/L and <4 pmol/L. Concentrations of intact PTH were determined using Quantitative ELISA (Roche Diagnostics, Cobas e602, Pleasanton, Calif.). Concentrations of calcium were determined using the Calcium Gen 2 kit on a Cobas c502 (Roche Diagnostics, Indianapolis, Ind.). All the tests were performed at ARUP Laboratories (Salt Lake City, Utah).

Method Validation

Method validation included of the evaluation of the imprecision, sensitivity, linearity, accuracy, recovery, carryover, and ion suppression, as well as establishing the reference intervals. Plasma pools used during the method validation were prepared from remaining aliquots of patient samples submitted for PTHrP testing to ARUP laboratories. An assessment of within and between run imprecision was performed by analyzing pools of human plasma samples containing endogenous PTHrP or supplemented with recombinant PTHrP (PeproTech). Concentrations of PTHrP in the samples were 4, 12, 48, and 398 pmol/L, which were analyzed in three replicates over seven days. In addition, three quality control (QC) samples were analyzed in routine runs over 20 days. All studies were approved by the Institutional Review Board of the University of Utah.

Limits of detection and quantification were evaluated by analyzing plasma samples containing progressively lower concentration of PTHrP. Four samples were prepared by dilution of a plasma pool containing 4.5 pmol/L with HEPES buffer. These samples were analyzed in triplicate over three days. Linearity of the method was evaluated by analyzing seven samples prepared by mixing in different proportions two plasma pools containing 8 and 580 pmol/L of PTHrP. The samples were analyzed in duplicate over two days. LOQ and upper limit of linearity were determined as the lowest and the highest concentrations, respectively, at which accuracy was within ±15%, imprecision was <20%, and a ratio of the mass transitions were maintained within ±30%. LOD was the lowest concentration at which chromatographic peaks were present in all mass transitions and signal to noise ratio was >7. Blank samples were injected after high standards to evaluate carryover potential of the method.

The method was compared with PTHrP RIA (Immunotech); samples used for the evaluation were remaining aliquots of patient plasma samples submitted to ARUP laboratories for routine testing. Three sets of plasma samples were used for the method evaluation: (1) samples previously analyzed for PTHrP by the Immunotech RIA (n=207), (2) samples containing elevated calcium (>1.05 mg/L) and low PTH (<15 pg/mL; n=88); and (3) samples with normal calcium and low PTH (<15 pg/mL; n=44). Difference in concentrations among the groups was evaluated using Wilcoxon rank-sum test.

Qualitative confirmation of PTHrP was assessed through the ratio of the concentrations determined from two mass transitions of the targeted peptide and the IS; ratio of the mass transitions outside of the ±30% range or presence of split peaks were considered as evidence of interfering peaks.

The affinity enrichment recovery was determined by performing enrichment of a plasma pool of patient samples containing 10 pmol/L of PTHrP. IS was added to three samples before sample preparation and to another three samples after the enrichment, and the remaining sample preparation was performed as described above. Differences between the observed concentrations of PTHrP in the pre- and post-enrichment spiked samples gave a measure of the recovery.

Sample dilution integrity was evaluated by analyzing a patient plasma sample containing 180 pmol/L of PTHrP. The sample was analyzed (in duplicate) with dilutions 3×, 5×, 10×, 20×, and 100×. The dilution was performed with a plasma sample containing 1.2 pmol/L of PTHrP.

The effects of lipemia, hemolysis, and icterus were evaluated by analyzing pools of 'normal' plasma samples containing 5 pmol/L of PTHrP and the same pool spiked with intra-lipid (1.1%), bilirubin (150 mg/L), and hemolyzed red blood cells (1.5 g/L). Concentrations observed in the samples were then compared.

Ion suppression was evaluated using a post column infusion method. A set of patient samples containing low concentrations of PTHrP was analyzed by the method, while the standard of the peptide YLTQETNK peptide (SEQ ID NO: 002) (100 ng/mL) was infused into the effluent of the analytical column. The chromatograms were inspected for signs of ion suppression.

The suitability of blood collection tubes was evaluated using six types of tubes with blood drawn from five volunteers. Blood was drawn into separate tubes, with each tube containing one of potassium EDTA, sodium heparin, lithium heparin, serum, serum separation, and Phe-Pro-Arg-chloromethylketone inhibitor tubes (PPACK, Haematologic Technologies, Essex Junction, Vt.). PTHrP concentrations observed in the samples were compared within each individual; samples were analyzed fresh and after storage in a refrigerator for 48 h. Stability was also evaluated by repeat analysis of patient samples collected in tubes containing PPACK inhibitor) processed on ice until aliquoted, then returned in −70° C. freezer and defrosted for the repeat testing.

A reference interval study for PTHrP was performed with samples from self-reported healthy adult volunteers without chronic diseases, 114 men (ages 20-58, median 33), and 122 women (ages 20-67, median 32). Body mass index (BMI) of the participants was calculated as weight (kg) divided by height (m) squared. Blood was collected in tubes with PPACK inhibitor, plasma was separated from blood cells within one hour, and the samples were stored at −70° C.

TABLE 2

Within-run, between-run, total imprecision

| Mean Concentration, pmol/L | Imprecision, % | | |
|---|---|---|---|
| | Within-run | Between-run/day | Total |
| 4.3 (pool of patient samples)* | 8.93 | 1.27 | 9.02 |
| 12.4 (pools of patient samples spiked with recombinant PTHrP)* | 6.70 | 6.63 | 9.42 |
| 47.8 (pools of patient samples spiked with recombinant PTHrP)* | 4.58 | 7.29 | 8.61 |
| 4.4 (pools of patient samples analyzed as QC)** | N/A | 13.4 | N/A |
| 11.8 (pools of patient samples analyzed as QC)** | N/A | 12.2 | N/A |

*data correspond to plasma samples containing PTHrP, analyzed in triplicate over 7 days.
**data correspond to QC samples (plasma samples containing PTHrP) analyzed over 20 days in single replicate per day.

Results

Figure 1B:
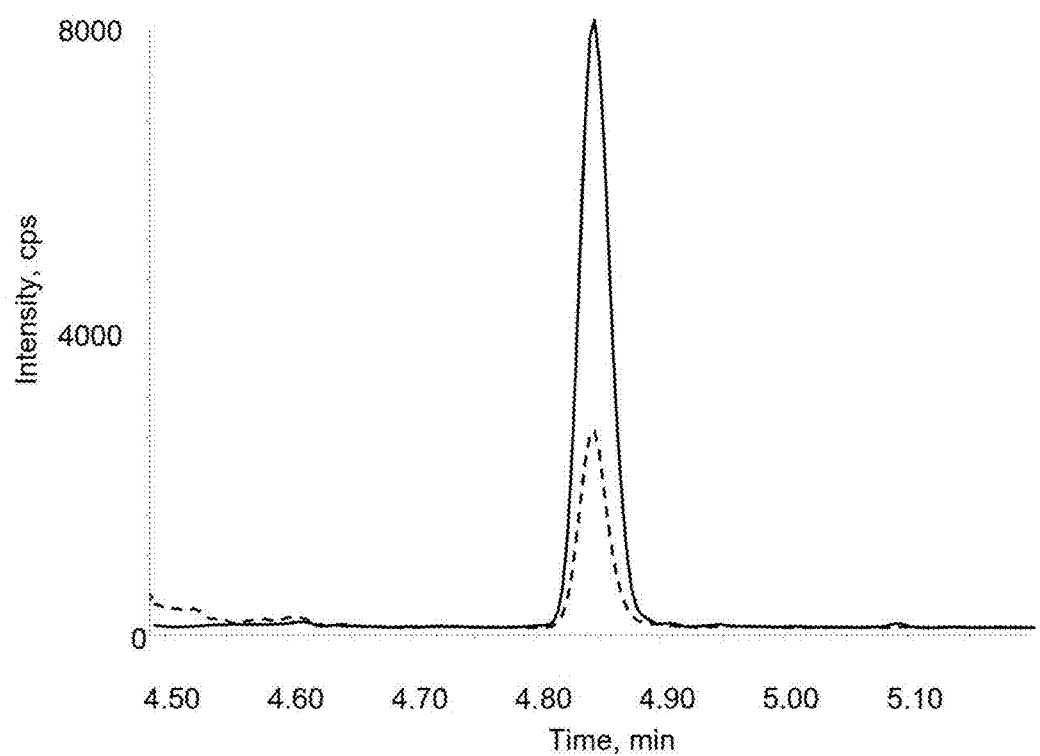
FIG. 1B is an MRM chromatogram of data in accordance with one example.
Figure 2:
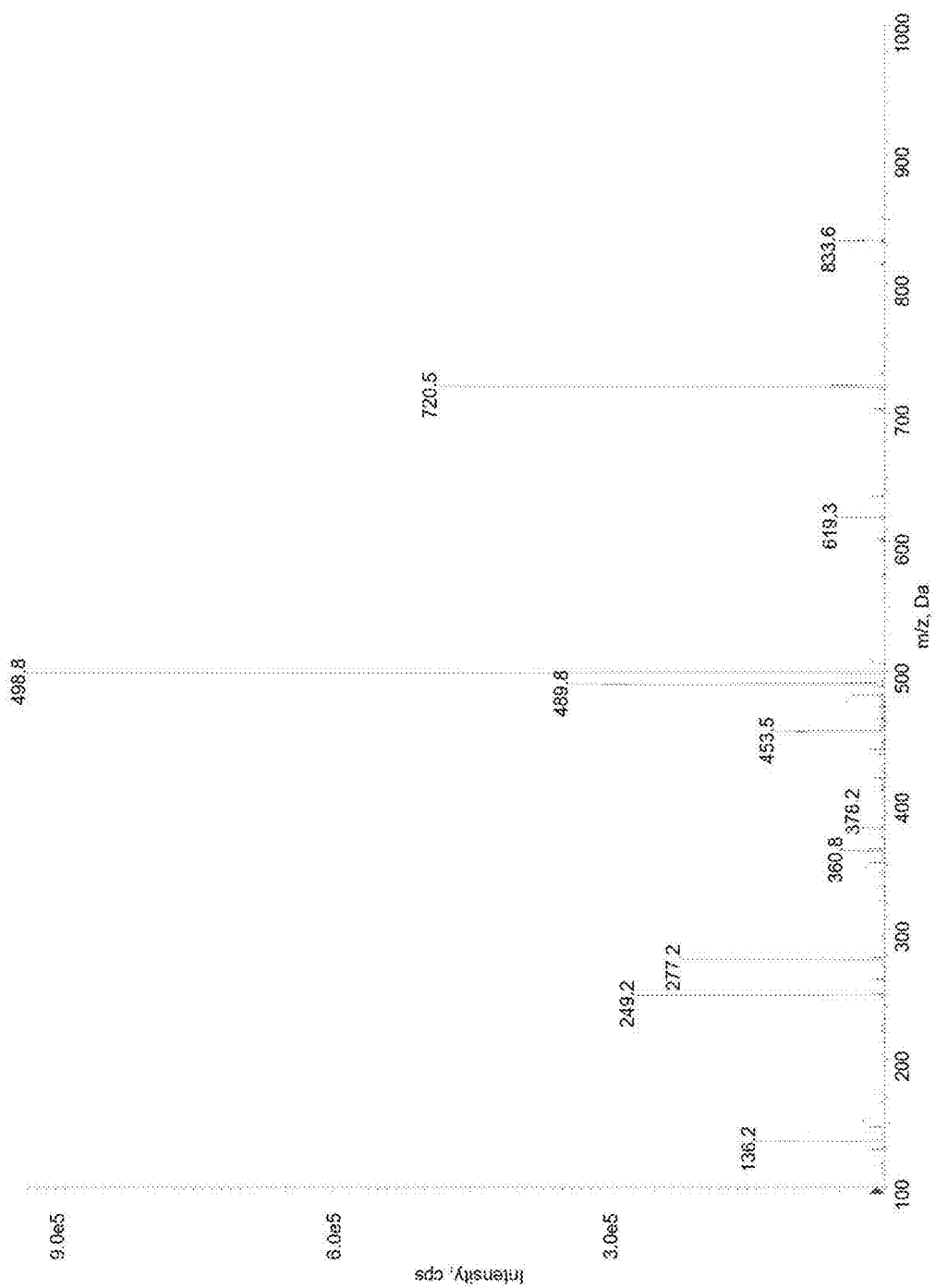
FIG. 2 is a product ion mass spectrum in accordance with one example.

Product ion mass spectrum of a PTHrP-specific peptide, YLTQETNK peptide (SEQ ID NO: 002), is shown in FIG. 2, and MRM chromatograms for a sample are shown in FIGS. 1A-B. Specifically, FIGS. 1A-B show MRM chromatograms of mass transitions of PTHrP (1A), and or IS (1B) in a patient sample containing 1.8 pmol/L PTHrP. Solid lines correspond to the primary mass transitions, and dashed lines correspond to the secondary mass transitions. The total assay imprecision at the evaluated concentrations was <10% (Table 2), the imprecision of PTHrP measurements in QC samples containing 4 and 12 pmol/L of PTHrP analyzed over 20 days was 13.4% and 12.2%, respectively, and the LOQ and LOD were 0.6 and 0.3 pmol/L, respectively. The method was linear up to 600 pmol/L, with inaccuracy at the highest concentration of 6.0%. No carryover was detected immediately after processing a sample containing 5,000 pmol/L of PTHrP. Method recovery was 98%, and the recovery of the immunoaffinity enrichment (IAE) was 70%. Concentrations observed in the samples from the dilution integrity experiment agreed with each other to within 7%.

Accuracy and imprecision of the method were evaluated using two ISs, the recombinant 15N-PTHrP (SEQ ID NO: 001) and the 'winged' labeled peptide DDEGRYL*TQETNKVETY (SEQ ID NO: 040), which were added to the samples before and after the affinity enrichment. When the winged peptide was added prior to the enrichment, it was binding to the antibody during the affinity enrichment. The imprecision of replicate measurements at four evaluated concentrations (9-50 pmol/L) was 21%, with a mean accuracy of 39% (data not shown). The higher biases were observed in samples containing higher concentrations of PTHrP.

As described above, PTHrP is known to be very unstable. In samples of four out of the five individuals, PTHrP concentration in samples collected in PPACK tubes were higher than in the other five types of tubes (mean difference 30%). After 48 hours of storage at 4° C., PTHrP concentrations in PPACK plasma were 39% lower than in the fresh samples (p=0.036), suggesting poor stability of PTHrP in the plasma containing PPACK inhibitor when stored at 4° C. Good stability was observed in samples defrosted for aliquoting on ice and then re-frozen immediately after the aliquoting. The presence of hemolysis, icterus and lipemia, did not affect the method performance; no ion suppression was observed at the retention time of the peptide.

Figure 3A:
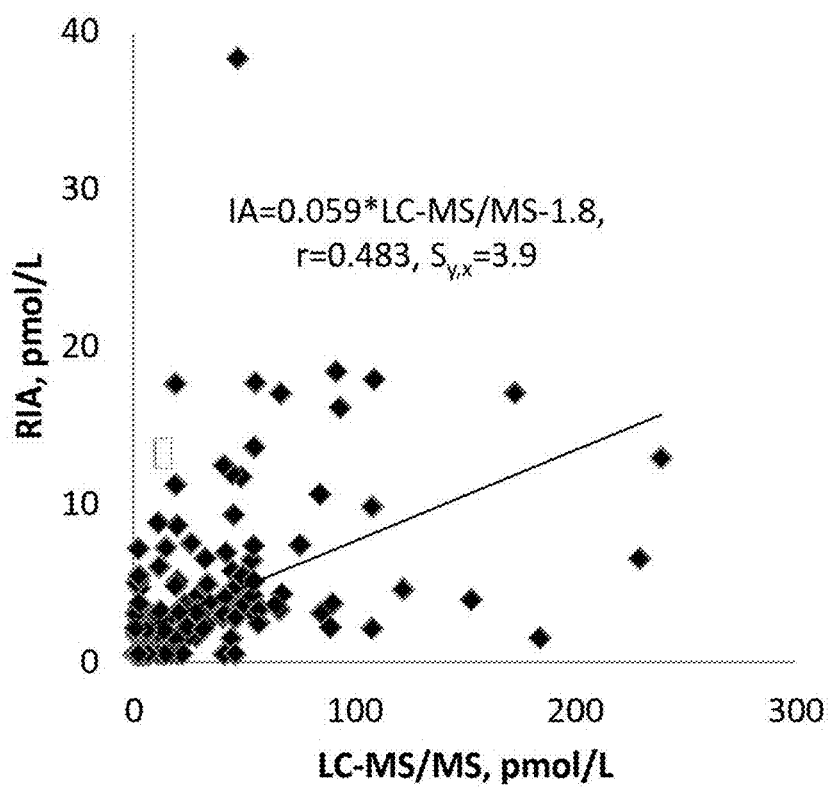
FIG. 3A is a graphical representation of data in accordance with one example.
Figure 3B:
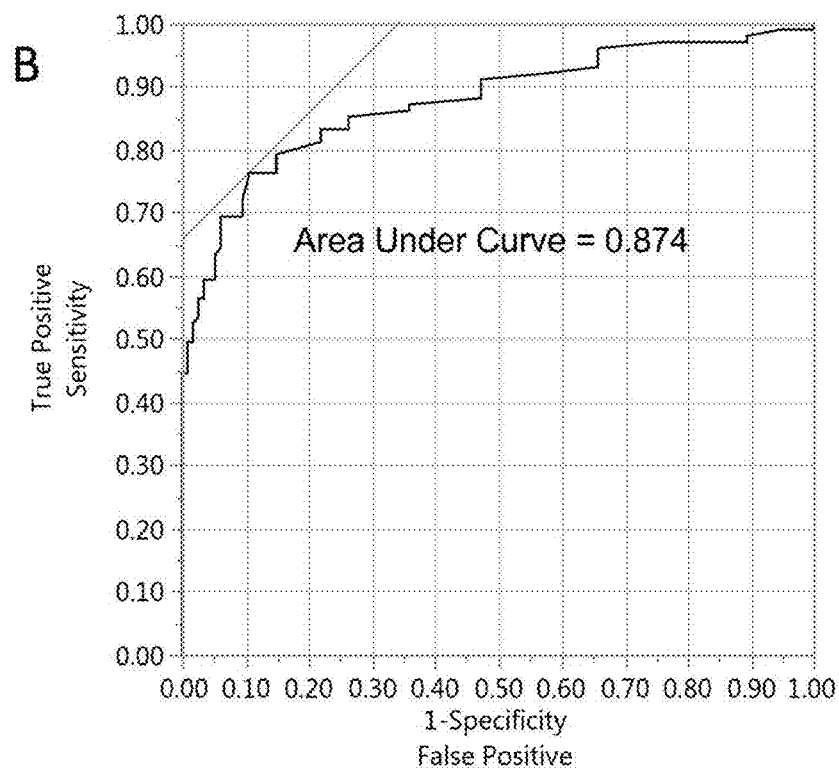
FIG. 3B is a graphical representation of data in accordance with one example.

The present LC-MS/MS method was compared with a commercial PTHrP MA kit (Immunotech). Deming regression equation for the comparison was IA=0.059*LC-MS/MS-1.8, n=207, r=0.483, $S_{y.x}$=3.9 (FIGS. 3A-B). FIG. 3A shows the LC-MS/MS method comparison with the MA assay for analysis of PTHrP in plasma samples (n=207), and FIG. 3B shows a ROC curve for the detection of increased PTHrP as a cause of hypercalcemia in a set of plasma samples from patients with hypercalcemia (n=91) and samples from self-reported healthy adults with no hypercalcemia (n=108).

Figure 5A:
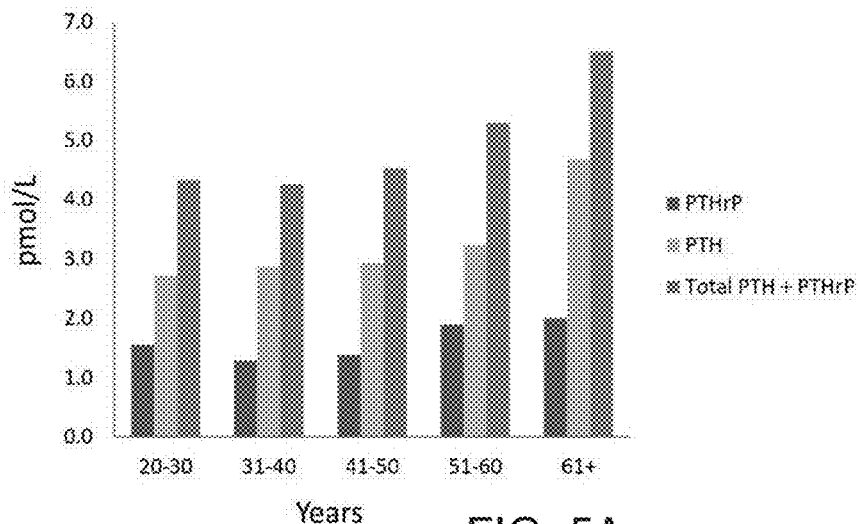
FIG. 5A is a graphical representation of data in accordance with one example.
Figure 5B:
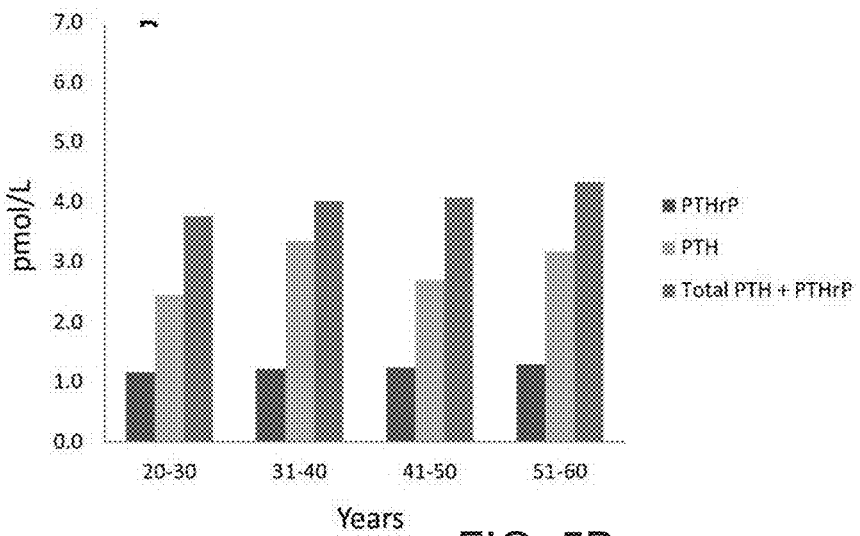
FIG. 5B is a graphical representation of data in accordance with one example.
Figure 7A:
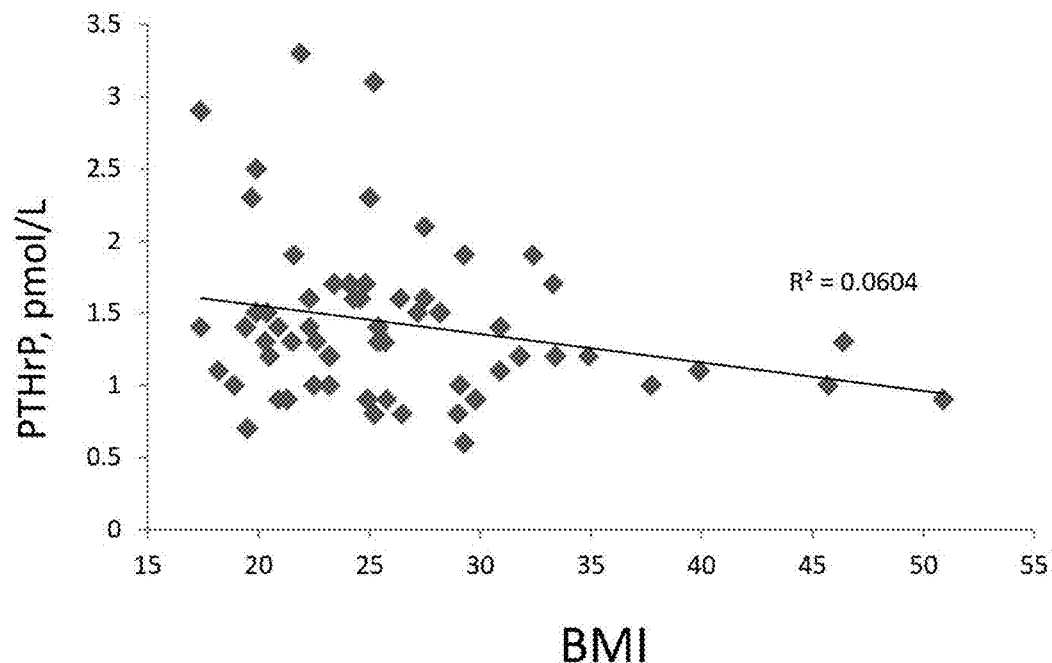
FIG. 7A is a graphical representation of data in accordance with one example.
Figure 7B:
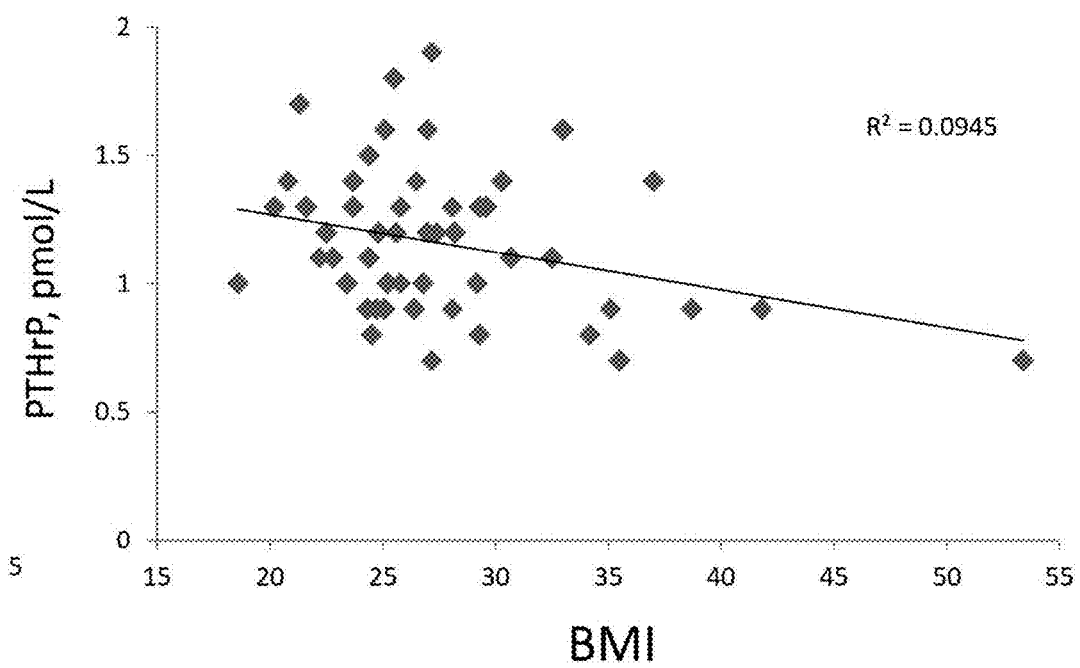
FIG. 7B is a graphical representation of data in accordance with one example.

Nonparametric reference intervals of PTHrP established with this method were 0.6-3.3 pmol/L and 0.6-2.2 pmol/L in adult women and men, respectively. Both PTH and PTHrP exert their action on Ca regulation in blood by binding to the same receptors; considering this, the distribution of PTHrP, (PTH+PTHrP), and the ratio of concentrations PTHrP/PTH was evaluated in plasma samples of healthy adults. FIGS. 4A-D show distributions of concentrations of PTHrP (A), PTH (B), PTH+PTHrP (C), and PTHrP/PTH (D) in apparently healthy women (n=120) and men (n=109). FIGS. 5A-B show the median concentrations of PTHrP, PTH, (PTHrP+PTH) and PTHrP/PTH ratio in healthy men (n=109)(B) and women (n=120)(A), arranged by decade of life. Reference intervals for PTH+PTHrP were 1.5-8.3 pmol/L in women and 1.2-8.2 pmol/L in men. Reference intervals for the PTHrP/PTH ratio were 0.2-1.4 in women and 0.2-1.0 in men. The data in Table 3 summarizes the median concentrations and distribution of the concentrations in men and women by decades of life.

observed in women (FIG. 7A, n=60) and men (FIG. 7B, n=53) with higher BMI (FIGS. 7A-B).

In order to assess performance of the LC-MS/MS assay, PTHrP in two sets of patient samples submitted for routine testing was analyzed. In the set of samples with high Ca and low PTH, 42% of samples had concentrations of PTHrP above the established reference intervals, and the PTHrP/PTH ratio was above the reference interval in all samples. The total concentration (PTHrP+PTH) was above the reference interval in 24% of samples. In the set of patient samples containing normal Ca and low PTH, 23% of samples had PTHrP concentrations above the reference interval.

Clinical performance of the assay and its ability to detect elevated PTHrP concentrations as a cause of hypercalcemia were evaluated by analysis of PTHrP in a set of plasma samples (n=199) biochemically characterized hypercalcemic (Ca>10.5 mg/dL and PTH<15 pg/mL; n=91) and a set of samples from self-reported healthy adults with concentrations of Ca and PTH within established reference intervals (n=108). Logistic regression analysis resulted in ROC (FIG. 3B) with AUC=0.874 (Chi Square test value for the model 113, p<0.0001). The data on the diagnostic utility of the assay are summarized in Table 4.

TABLE 3

Concentrations of PTHrP, PTH plus PTHrP, and PTHrP/PTH in plasma samples of self-reported healthy adults by age group.[a]

| Age, years | n | Median age, years | PTHrP, pmol/L | PTH + PTHrP, pmol/L | PTHrP/PTH |
|---|---|---|---|---|---|
| Women | | | | | |
| 20-30 | 52 | 25.5 | 1.6 (0.7-4.2) | 4.3 (1.3-7.4) | 0.60 (0.2-1.86) |
| 31-40 | 37 | 34.0 | 1.3 (0.6-3.5) | 4.3 (2.6-8.4) | 0.47 (0.17-1.83) |
| 41-50 | 16 | 45.0 | 1.4 (0.2-2.0) | 4.5 (0.25-9) | 0.49 (0.19-0.80) |
| 51-60 | 14 | 56.5 | 1.9 (1-3.4) | 5.3 (3.6-6.9) | 0.53 (0.23-1.16) |
| >61 | 4 | 63.0 | 2.0 (1-3.3) | 6.5 (4.5-9.3) | 0.59 (0.15-0.73) |
| Breastfeeding | 6 | 34.5 | 2.4 (1.7-3.2) | 5.3 (3.5-7.8) | 0.79 (0.6-1.0) |
| Men | | | | | |
| 20-30 | 35 | 27.0 | 1.2 (0.6-2.0) | 3.8 (1.5-8.0) | 0.49 (0.16-0.87) |
| 31-40 | 42 | 33.0 | 1.2 (0.6-2.1) | 4.3 (1.0-10.1) | 0.35 (0.14-1.07) |
| 41-50 | 24 | 43.5 | 1.2 (0.6-2.4) | 4.1 (0.6-5.7) | 0.45 (0.21-1.0) |
| 51-60 | 14 | 53.0 | 1.3 (0.8-2.4) | 4.3 (2.2-10.0) | 0.39 (0.14-0.76) |

[a]Data are median (central 95% concentration) unless noted otherwise

Figure 6:
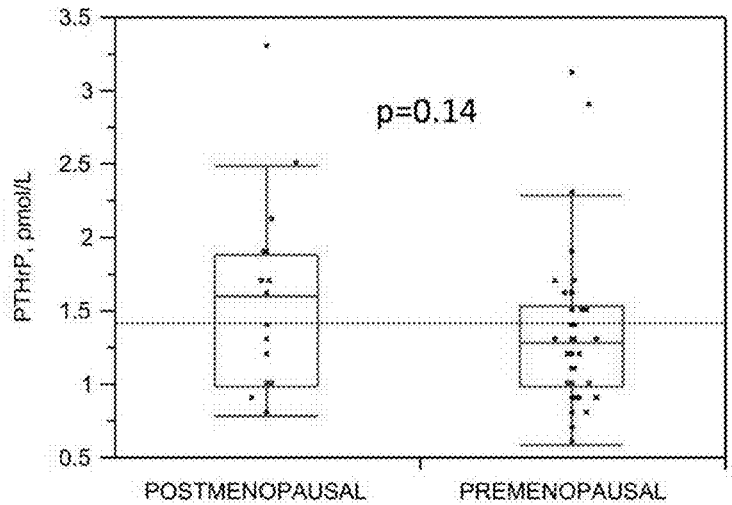
FIG. 6 is a graphical representation of data in accordance with one example.

No statistically significant difference in distribution of the concentrations and the ratios was observed among age groups in men. In women, however, PTHrP concentrations were significantly higher in 20-30 year (p=0.0025) and older than 50 years (p=0.006), as compared to the 30-50-year group (Table 3). Total concentration of PTH+PTHrP was higher in women older than 50 years as compared to the younger women (p=0.0033). In 20-30-year-old women, the ratio of PTHrP/PTH was significantly higher than in the rest of the age groups (p=0.0048). In postmenopausal women, PTHrP concentrations were higher than in pre-menopausal women (p=0.14), as is shown in FIG. 6. Specifically, FIG. 6 shows the distribution of PTHrP concentrations in premenopausal (n=15) and postmenopausal (n=45) women. FIGS. 7A-B show that lower concentrations of PTHrP were

TABLE 4

Diagnostic utility of the LC-MS/MS test for PTHrP.

| Cutoff concentration, pmol/L | Positive predictive value | Negative predictive value | Clinical sensitivity | Clinical specificity | Diagnostic efficiency |
|---|---|---|---|---|---|
| 1.8 | 0.88 | 0.80 | 0.76 | 0.89 | 0.82 |
| 2.3 (upper normal for men) | 0.94 | 0.73 | 0.59 | 0.96 | 0.79 |
| 3.3 (upper normal for women) | 0.98 | 0.67 | 0.45 | 0.99 | 0.73 |

Discussion

The present methodology analyzed PTHrP by quantitating PTHrP-specific peptide released during tryptic digestion. Peptide YLTQETNK (SEQ ID NO: 002) is in the middle of the PTHrP sequence; while its concentration does not represent the concentration of bioactive PTHrP, it serves as a marker of the rate of PTHrP biosynthesis.

The example approach described herein utilizes immunocapture of PTHrP from plasma samples followed by proteolytic digestion (e.g. trypsin), while it is bound to the antibody conjugated to magnetic beads, followed by the direct analysis of the digests using triple quadrupole MS. The on-bead digestion used in this method allowed faster analysis without peptide elution, reduction and alkylation prior to the digestion. Considering that the enrichment takes place on the protein level, accurate quantitation of PTHrP requires careful selection of the IS. Two stable isotope labeled IS were evaluated, a 'winged' labeled peptide (SEQ ID NO: 040), and recombinant $^{15}$N PTHrP (SEQ ID NO: 001). The 'winged' IS provided partial improvement in the performance, while the accuracy of quantitation substantially improved with the use of the recombinant $^{15}$N PTHrP as the IS.

The YLTQETNK peptide used in this method is unique to PTHrP, has no homology with any other tryptic fragments of human proteins, and is a specific surrogate marker for quantitation of PTHrP. Among over 8,000 analyzed patient samples, <2% of samples were observed with a ratio of the mass transitions outside of 30% of the expected range among the samples contained >2 pmol/L of PTHrP.

PTHrP in plasma samples is unstable and undergoes rapid degradation. Out of the evaluated types of blood collection tubes, PTHrP concentrations were the highest in the tubes with PPACK inhibitor (analyzed immediately after defrosting). After the samples were stored refrigerated for 48 h, PTHrP degraded to concentrations similar to those observed in the other evaluated types of collection tubes. The among-individuals variation in the reduction of PTHrP concentration in samples analyzed fresh and after storage could be related to the differences in concentrations of endogenous proteases causing PTHrP degradation. The observed data suggest that PTHrP degradation begins at the time of blood collection and plasma separation, and suggest the necessity to draw blood in tubes containing PPACK inhibitor.

In samples from the volunteers collected in tubes with a PPACK inhibitor, PTHrP concentrations were above the LOQ of the method in 99.6% of samples (FIGS. 4A-D), with higher concentrations observed in women than in men. In women, concentrations were highest in breastfeeding and postmenopausal women as compared to the other groups of healthy adults. There was no association observed in men between PTHrP concentrations and age. Gaussian distribution of the concentrations in samples of healthy individuals suggests tight regulation of PTHrP. Considering that PTHrP plays a role in development of mammary glands, lactation, pregnancy, and osteoporosis, it is expected that PTHrP concentrations should be higher in women than in men, which is consistent with the present data. Higher concentrations of PTHrP were observed in individuals with lower BMI (FIGS. 7A-B), and in postmenopausal women (FIG. 6).

Based on current knowledge, in health, Ca in blood is regulated by PTH, and PTHrP in blood of healthy individuals is often undetectable. The present data demonstrate that PTH and PTHrP are present in blood at comparable concentrations. Since both hormones bind to the same receptors, it is likely that they are both responsible for Ca regulation, and the total concentration of PTHrP+PTH (or possibly a weighted sum of PTHrP and PTH) could be more representative of the status of Ca regulation, rather than concentration of PTH alone. Data in Table 3 and FIGS. 4A-D show distributions of the total and relative concentrations of PTHrP and PTH in plasma samples from healthy adults. The present data suggest that concentrations of PTHrP and PTHrP+PTH are higher in postmenopausal women compared to men and premenopausal women. These observations could provide a partial explanation of the high prevalence of osteoporosis in postmenopausal women with low BMI.

The ability of the method to identify PTHrP as a cause of hypercalcemia was evaluated by analyzing PTHrP in pathologic patient plasma samples. It was hypothesized that, in many of the patents with unexplained HC that tested negative for PTHrP by the RIA, PTHrP was not detected because of poor performance of the RIA. In a set of 88 samples of patients with HC, 42% of samples had elevated PTHrP; the PTHrP/PTH ratio was above the reference interval in all samples of the set. In another set of plasma samples from patients with normal Ca and low PTH, PTHrP concentrations were above the established reference interval in 23% of patients. Considering that Ca is tightly regulated and its concentration in health is maintained within a narrow physiological range, the observed Ca concentrations in these two sets of samples could not be explained by PTH alone. One possibility of the HC in some of the patients from the first cohort and normocalcemia in the second cohort could be caused by elevation of PTHrP.

Data on the diagnostic utility of the assay are summarized in Table 4. The highest diagnostic efficiency (0.82) was observed at PTHrP cutoff concentration of 1.8 pmol/L, the highest positive predictive value (0.98) and clinical specificity (0.99) were observed at the upper cutoff concentration for women (3.3 pmol/L). The above data suggest robust performance of the assay and its high clinical value.

In a review of causes of hypercalcemia, Jacobs and Bilezikian stated that in many cases HC is not associated with elevated PTHrP. This observation could be related to the poor performance of available PTHrP assays, which tend to underestimate PTHrP concentration, resulting in a very low positivity rate in samples from patients clinically suspected of HC. Because of the poor performance, previously available methods were not able to reliably measure PTHrP in healthy individuals, resulting in the assumption that PTHrP is not present in circulating blood in health. The present study identified a large number of patient samples with substantial disagreement in the results between the Immunotech RIA and this LC-MS/MS assay (FIGS. 3A-B). In a subset of 207 patient samples analyzed for the method comparison, 18.4% of samples had PTHrP concentration above the cutoff of the RIA, while based on the LC-MS/MS assay, 53.6% of samples had concentration above the LC-MS/MS reference intervals.

While in routine use among consecutively analyzed samples using RIA (n=1376), the positivity rate was 1.9%. Among consecutively analyzed samples using the present LC-MS/MS assay (n=1705), the positivity rate was 26.6%. In the above sets of samples analyzed by RIA, concentrations were below the LOQ in 95.6% of the samples, as opposed to only 2.0% in the LC-MS/MS samples. The above data suggest that in many patients with clinical symptoms of HC, PTHrP was not detected by RIA, not because the concentrations were too low, but because of the poor performance of the RIA. Considering that samples typically submitted to reference laboratories for measurement of PTHrP are from patients in whom HC was clinically suspected, the observed low positivity rate of the RIA (<2%) suggests that the RIA produces falsely low results in many of the samples. Based on the present data, elevated concentrations of PTHrP in samples of patients with suspected HC are more common than was stated previously.

Considering the difference in half-lives of PTH and PTHrP (~4 min and few hours, respectively), and that both PTH and PTHrP are involved in Ca regulation, the total and relative concentrations of PTHrP and PTH could be of importance for the assessment of Ca regulation in patients with signs of osteoporosis, osteomalacia, and unexplained hypercalcemia. Data on the distribution of the total concentration of PTH+PTHrP and the ratio of concentrations PTHrP/PTH in samples from healthy adults (Table 3 and FIGS. 4A-D) demonstrate relatively narrow distributions of the concentrations and the ratios. Since abnormal secretion of PTHrP could be caused by tumors, this PTHrP method may potentially be used as a screening test for early detection of PTHrP-secreting malignances and conditions associated with abnormal Ca regulation.

While the focus of the present disclosure deals with the quantitative analysis of PTHrP in plasma samples, immunoaffinity enrichment and on-beads digestion used in this method could be generally applicable to the LC-MS methods for other protein biomarkers.

While the forgoing examples are illustrative of the principles of invention embodiments in one or more particular applications, it will be apparent to those of ordinary skill in the art that numerous modifications in form, usage and details of implementation can be made without the exercise of inventive faculty, and without departing from the principles and concepts of the disclosure.

What is claimed is:

1. A method of measuring parathyroid hormone-related peptide (PTHrP) in a biological sample, comprising:
    preparing the biological sample, wherein preparing further comprises:
        extracting PTHrP peptides from the biological sample;
        mixing a PTHrP sequence-derived isotope-labeled internal standard (IS) with the PTHrP peptides;
        proteolytically digesting the PTHrP peptides and the IS to produce a digestion product; and
        chromatographically separating the digestion product; and
    selecting and subjecting a chromatographic peak of the separated digestion product to tandem mass spectrometry to determine the amount of a target peptide, wherein the sequence of the target peptide is YLTQETNK (SEQ ID NO: 002) and the sequence of the IS is YLTQETNK (SEQ ID NO: 002).

2. The method of claim 1, wherein the IS is isotope-labeled in at least one amino acid with at least one $^{15}$N.

3. The method of claim 2, wherein the IS is isotope-labeled in all amino acids with $^{15}$N at all N atoms.

4. The method of claim 3, wherein mass transitions characteristic of the IS are about m/z 504→729 and about m/z 505→730.

5. The method of claim 3, wherein mass transitions characteristic of the IS are m/z 504.25→729.35 and m/z 504.75→730.25.

6. The method of claim 1, wherein mass transitions characteristic of the target peptide are about m/z 499→720 and about m/z 499→721.

7. The method of claim 1, wherein mass transitions characteristic of the target peptide are m/z 498.75→720.35 and m/z 499.25→721.35.

8. The method of claim 1, wherein the amount of the target peptide is detectable to a sensitivity of at least 0.5 pmol/L.

9. The method of claim 1, wherein preparing the biological sample is performed in 2 hours or less in order to minimize PTHrP degradation.

10. The method of claim 1, performed without a reduction reaction and without an alkylation reaction.

11. The method of claim 1, wherein extracting PTHrP peptides from the biological sample further comprises an affinity extraction selective for PTHrP.

12. The method of claim 11, wherein the affinity extraction is antibody affinity extraction.

13. The method of claim 12, wherein the antibody is coupled to magnetic beads.

14. The method of claim 11, wherein the affinity extraction is aptamer affinity extraction.

15. The method of claim 1, wherein proteolytically digesting is by trypsin digestion.

16. The method of claim 1, wherein the IS comprises at least one amino acid having at least three incorporated isotopic atoms independently selected from the group consisting of $^{13}$C, $^{15}$N, and $^{2}$H.

* * * * *